(12) United States Patent
Akiyama

(10) Patent No.: US 7,002,676 B2
(45) Date of Patent: Feb. 21, 2006

(54) APPEARANCE INSPECTION APPARATUS AND THE METHOD OF INSPECTING THE SAME

(75) Inventor: Yoshihiro Akiyama, Kanagawa-ken (JP)

(73) Assignee: Saki Corporation, (JP)

( * ) Notice: Subject to any disclaimer, the term of this patent is extended or adjusted under 35 U.S.C. 154(b) by 200 days.

(21) Appl. No.: 10/762,144

(22) Filed: Jan. 20, 2004

(65) Prior Publication Data

US 2004/0212797 A1    Oct. 28, 2004

(30) Foreign Application Priority Data

Jan. 20, 2003    (JP) .............................. 2003-011656

(51) Int. Cl.
    *G01N 21/00*    (2006.01)
(52) U.S. Cl. .................................. 356/237.2
(58) Field of Classification Search ................ None
    See application file for complete search history.

(56) References Cited

U.S. PATENT DOCUMENTS

| | | | |
|---|---|---|---|
| 5,197,105 A * | 3/1993 | Uemura et al. ............. 382/147 |
| 6,211,899 B1 * | 4/2001 | Yoshida ....................... 347/250 |
| 6,424,735 B1 * | 7/2002 | Freifeld ...................... 382/154 |
| 6,437,312 B1 * | 8/2002 | Adler et al. ................. 250/216 |
| 6,552,783 B1 * | 4/2003 | Schmidt et al. .......... 356/237.4 |
| 6,560,024 B1 | 5/2003 | Akiyama et al. |
| 2004/0012775 A1 * | 1/2004 | Kinney et al. ........... 356/237.2 |

* cited by examiner

*Primary Examiner*—Michael P. Stafira
(74) *Attorney, Agent, or Firm*—Anderson Kill & Olick, PC

(57) ABSTRACT

An appearance inspection apparatus and method using at least one telecentric lens, although at least two is preferred and at least a corresponding number of line sensors arranged in parallel with the image capture direction for inspecting a large circuit board. When two lenses are used two images are formed, which partially overlap each other. If image data for one line is captured in this state, a scanning head having two sets of telecentric optical systems move one line at a time in the driving direction. By repeating the same steps, data for two image segments which partially overlap throughout the entire line of board are obtained. The two image segments are synthesized after displacement of positions when colors in the overlapping portion of the two pieces of images are corrected. Inspection of board is then performed based on the combined image.

6 Claims, 9 Drawing Sheets

APPEARANCE INSPECTION APPARATUS AND THE METHOD OF INSPECTING THE SAME

TECHNICAL FIELD

The present invention relates to appearance inspection technology for inspecting electronic circuit boards. More specifically, it relates to an appearance inspection apparatus that scans the surface of an electronic board to detect defects and to a method of inspecting the appearance of an electronic circuit board.

RELATED ART

In the manufacture of electronic circuit boards having densely packed electronic components an inspection step is used to locate defects. The recent trend in high-density packaging demands accuracy in alignment of the circuit components on the order of several tens of microns. Along with a high demand for IT related equipment, particularly, portable equipment represented by cellular phones, a new demand for high speed packaging has been growing for years. These demands have made it extremely difficult to find defects on a circuit board on which components are densely packed. These demands have also outdated the contact type testing method utilizing probes such as the In-Circuit Tester (ICT) of conventional technology since the latest packaging involves dense packaging of small components of different heights, which gave rise to a demand for non-contacting type appearance inspection apparatus utilizing image discrimination technology.

The non-contacting type appearance inspection apparatus of this type must capture an image of the high-density packaging conditions on the surface of the circuit board to accurately detect defects. This involves a very long inspection time period to meet the inspection specification demands. The time consuming inspection process cancels the benefits of reduced packaging time for high-demand integrated circuits. This might delay shipments of products and cause electronics manufacturers to lose their competitive edge. This problem necessitated the development of an appearance inspection apparatus that can inspect components quickly and accurately.

Conventional appearance inspection apparatus will scan a board surface by means of a line sensor to read the image thereof and perform inspection, using data from the captured image. The index of packaged components on the board may be of the order of several tens of microns in size. Accordingly a high-density line sensor must be used. The CCD line sensor that is currently commercially available will read 5,000–10,000 pixels at a maximum, corresponding to detection at the 25 micron level, which limits the line sensor's reading to within a width range of 25 cm. To obtain the entire image of a larger board, the image of the board surface must therefore be split into multiple pieces because the line sensor is unable to read the image of the entire board at once. An appearance inspection apparatus that captures the image of the circuit board surface in two pieces providing partial overlap such that the two image pieces can be synthesized by putting them together is taught in Japanese Unexamined Patent Publication (Kokai) No. 2002-181729.

PROBLEMS TO BE SOLVED

If the appearance inspection apparatus involves splitting an image into multiple segments, the inspection apparatus must inspect the two image segments across the matching border. Such an inspection requires high precision matching technology on the order of several tens of microns, which further demands complicated analysis. The two image segments may be synthesized by putting the two image segments together before inspection. Nevertheless, the use of multiple lenses is susceptible to subtle aberrational differences of different lenses. As a result, positions of markings or color data do not match across the border of the two image segments. Two image segments thus do not correspond to each other near the border.

The present invention addresses the above problems of inspecting multiple images scanned from a circuit board. Another objective of the present invention is to provide an appearance inspection technology that allows inspection of the entire electronic board utilizing line sensors having a read-out width limitation.

SUMMARY OF THE INVENTION

The present invention relates to an appearance inspection apparatus comprising: a scanning head for scanning the surface of an electronic board to be inspected, to capture an image thereof and a main unit for performing an inspection based on the captured image. The scanning head further comprises: multiple sets of a telecentric lens and a one-dimensional sensor, with each arranged along an image capturing line. The telecentric lens forms images from catoptrical light reflected from the board surface; the one-dimensional sensor capturing reflected light. Each one-dimensional sensor captures an image of the board to be inspected, thereby providing a partially overlapping portion. The main unit further comprises: an image processing unit that puts together multiple images captured by each of the line sensors after calibrating pixel data in the overlapping portion; and an analysis unit that inspects an image segment, with reference to a given evaluation standard to determine pass or failure for each inspection item.

The image processing unit includes a color correction unit that corrects color convergence occurring in color data in the overlapping portion. Alternately, the color correction unit may adjust a color correction table of a second telecentric lens with reference to a color correction table of a first telecentric lens such that color data of pixels in the overlapping portion matches the color data from the first telecentric lens. Color correction data required for correcting chromatic aberrations of said telecentric lenses at the edge thereof may be generated in advance such that color convergence of the overlapping portion is corrected based on the color correction table image captured by the scanning head.

Images free of color convergence are thus obtained before the overlapping portions are put together. An accurate inspection across the border of image segments is thus made possible.

The image processing unit further comprises a position correction unit for aligning overlapping portions of a captured image based on reference data included in the overlapping portion. The reference data represents multiple subject points on the body or board to be inspected. Mismatching of positions of these subject points may be corrected during matching of the images to accurately put together the overlapping portions of the two images. The subject points on the body to be inspected include electronic components, guiding line patterns, through holes, names of components, model number, and the standard name printed on the board, and the like that can be matched on a synthesized image.

Another aspect of the present invention is a method of inspecting the surface appearance of a circuit board. The method of inspecting appearance comprises: capturing images of a body to be inspected utilizing multiple telecentric lenses in such a manner that the resulting multiple images partially overlap; synthesizing the multiple images after correcting color convergence appearing in the overlapped portion; and performing a given inspection based on the synthesized image.

DETAILED DESCRIPTION OF THE INVENTION

Figure 1:
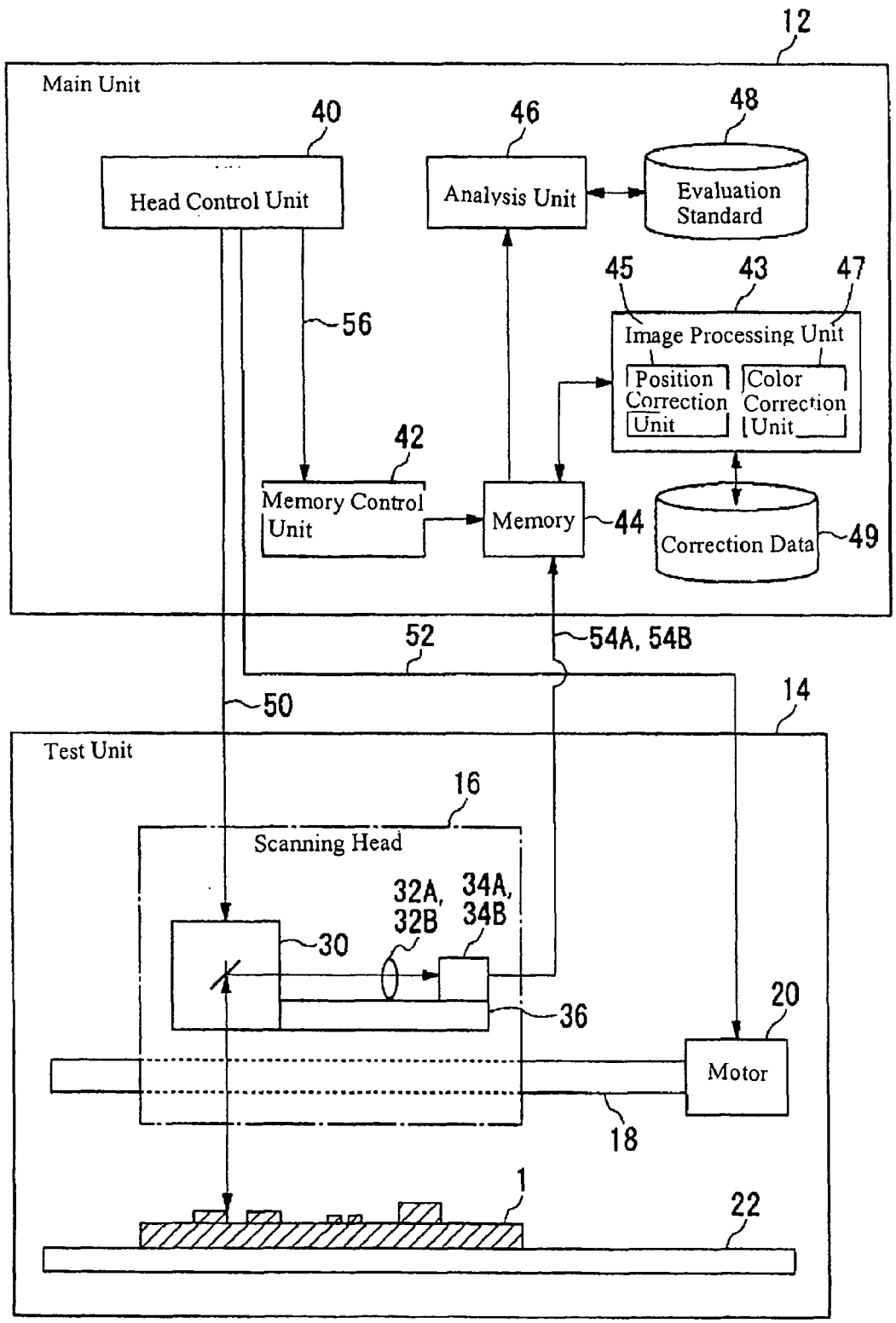
FIG. 1 is a configuration illustrating one embodiment of the appearance inspection apparatus of the present invention.

FIG. 1 is a configuration illustrating a preferred embodiment of the appearance inspection apparatus 10 of the present invention. This apparatus scans the surface of a body to be inspected using line sensors to form an overall image and discriminates the overall image to determine if defects exist. By moving a scanning head, as will be described hereafter, perpendicular to the image capturing line of the line sensor, an overall image of the board is obtained line by line. The overall image of the board surface is finally obtained as a result of the one-dimensional motion of the scanning head. Another type of appearance inspection apparatus repeats the two dimensional move-and-stop cycle over the inspection surface to spot-capture the image thereof. This type usually requires a complicated inspection mechanism and a long inspection time. The one-dimensional sensor of this embodiment is more advantageous in that it is free from the above drawbacks. An appearance inspection apparatus utilizing a one-dimensional sensor is taught by Applicant in Japanese unexamined patent publication (Kokai) No. H08-254500 the description being incorporated herein by reference.

In FIG. 1, appearance inspection apparatus 10 comprises: a main unit 12 and a test unit 14. A supporting base 22 is provided under the test unit 14, where circuit board 1, which is a body to be inspected, is mounted. A scanning head 16, a stepping motor 20 which moves the scanning head 16, and a guide 18 (e.g. linear guide) which holds scanning head 16 in position relative to the motor 20 are supported above the circuit board.

Scanning head 16 has a lighting unit 30, at least one telecentric lens, although at least two telecentric lenses, 32A and 32B are preferred as is shown in FIG. 1, and at least a corresponding number of line sensor(s) 34A and 34B. These members are secured to a frame 36 in the scanning head 16. As described later, a set of telecentric lenses, 32A and 32B, and a set of line sensors, 34A and 34B, are arranged along the image capture line such that the images captured by line sensors 34A and 34B have an overlapping portion parallel to the image capture line.

Lighting unit 30 is conventional and includes a vertical light source, a sidelong light source, and a half mirror and the like built therein (not shown). As shown by the arrows in FIG. 1, the light reflected vertically upward from board 1 is guided to telecentric lenses 32A and 32B via a half mirror 33, passes through telecentric lenses 32A and 32B, and is input to line sensors 34A and 34B, which are one-dimensional CCD sensors. Each of the two line sensors, 34A and 34B, captures an image of board 1 line by line, and output image data 54A and 54B to the main unit 12. Telecentric lenses, 32A and 32B, and line sensors, 34A and 34B, are hereinafter referred to as the telecentric optical system.

Main unit 12 controls the apparatus as a whole. The hardware identified in the main unit 12 is conventional. A software program having an appearance inspection function may be loaded onto the memory 44. FIG. 1 depicts a functional block actualized by interaction between hardware and software. It is apparent to one of ordinary skill in the art that the functional block may be actualized by hardware only or software only, or a combination of hardware and software.

Head control unit 40 of main unit 12 first supplies a lighting control clock 50 to lighting unit 30 and alternately lights up the vertical source and sidelong light source in the lighting unit 30. Head control unit 40 further outputs motor control signal 52 to motor 20 and test start signal 56 to memory control unit 42. Motor control signal 52 controls steps of motor 20 and moves scanning head 16 to the edge of board 1, when inspection begins. Using this as the initial position, scanning head 16 captures the image of one line every time it moves one line. Memory control unit 42 controls writing of image data, 54A and 54B, in memory 44 in syncopation with the test-start signal 56. Afterwards, image data, 54A and 54B, are recorded in memory 44 line by line. Image data, 54A and 54B, obtained under vertical lighting and that obtained under side lighting are interleaved line by line before being input into memory 44. As all lines are captured, one appearance inspection image captured by vertical lighting and the other appearance inspection image captured by side lighting are separately created and stored in memory 44.

Image processing unit 43 produces correction data and synthesizes the images. Position correction unit 45 reads out image data from memory 44 containing the image of the calibration board described later, detects positional deviations of ID markings on a calibration board together with the magnitude of the deviation, produces a position correction table for correcting aberrations of the telecentric optical system, and stores the correction table in correction data memory unit 49. In addition, color correction unit 47 reads out image data of a gray scale chart described later from memory 44 and creates a color correction table required for correcting chromatic aberration of the telecentric optical system, which is also stored in correction data memory unit 49.

During image synthesis, position correction unit 45 reads out image data, 54A and 54B, of board 1 from memory 44 and corrects distortions appearing in the overall image utilizing the position correction table stored in correction data memory unit 49 in advance. Position correction unit 45 further synthesizes two image segments by matching the overlapping portion and putting the borders together in a manner described later. Further, color correction unit 47 corrects color convergence in the overlapping portion utilizing the color correction table previously stored in Correction data memory unit 49 and stores the synthesized corrected image in memory 44. Memory 44 provides a large capacity memory region to store the image of the overall board as single image data.

Analysis unit 46 reads the synthesized image data from memory 44 and determines pass or failure for each of the inspection items with reference to the evaluation standard previously recorded in evaluation standard memory unit 48. Items inspected by the vertical light test include displacement of components, missing components and wetting of soldering. Items inspected by the side light test include the presence or absence of a soldering bridge, wrong components, and reversed polarity. In the vertical test, "wetting of soldering" is determined as follows: when a uniform dark spot appears around electrodes of components, wetting of soldering is good; when a dark spot appears away from electrodes; wetting of soldering is poor. In the latter case, it is most likely that solder is not melted on electrodes but left on the land, thereby looking like a short convexity. Whatever the situation, the point is that an evaluation standard or a standard image, associated with pass or failure of components mounted on board 1, is recorded in evaluation standard memory unit 48 in advance, and pass or failure is determined with reference to the evaluation standard or standard image.

Figure 2:
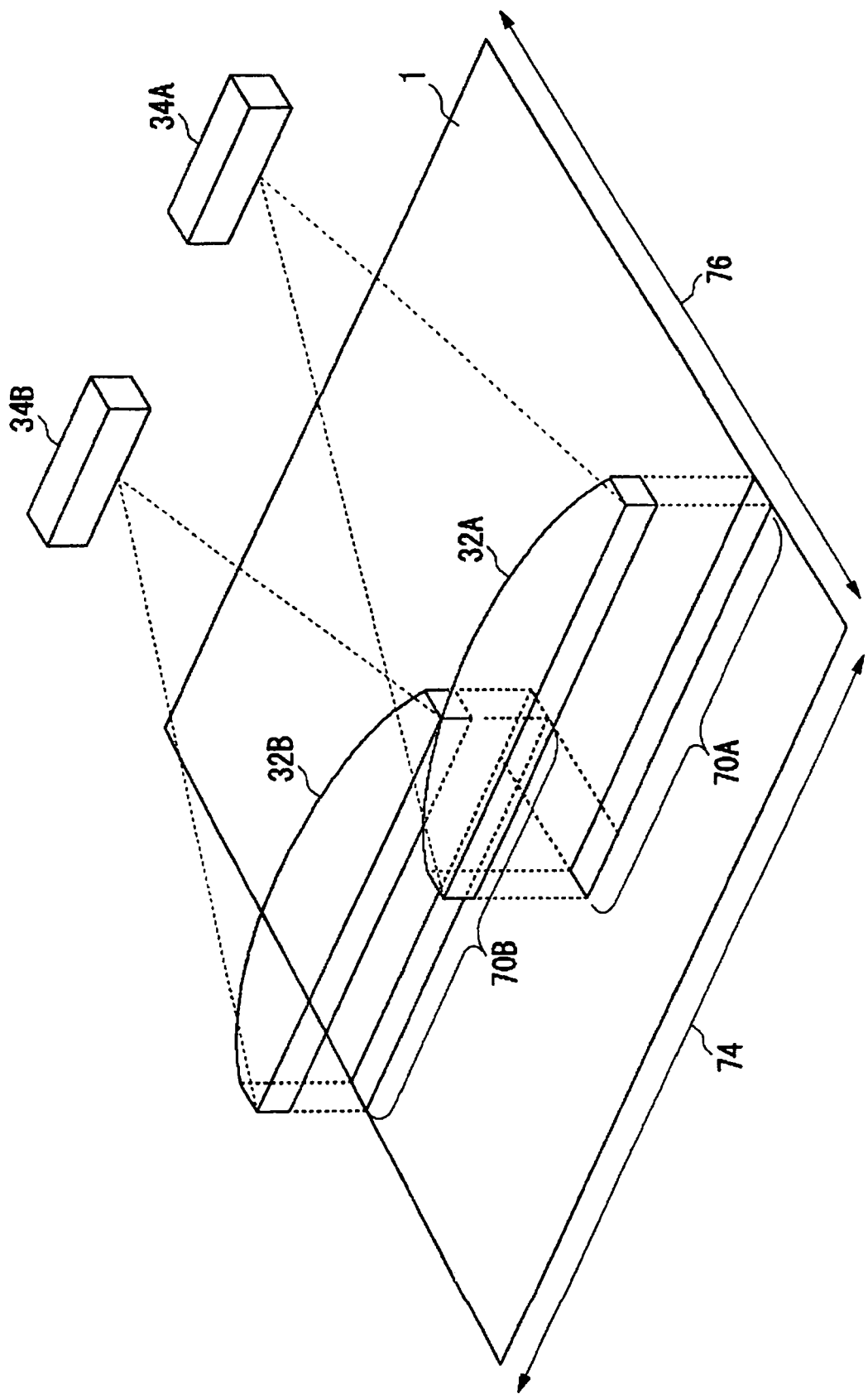
FIG. 2 is a diagram illustrating scanning of the board surface utilizing two line sensors in a scanning head.

FIG. 2 is a diagram showing scanning of a circuit board utilizing the two line sensors 34A and 34B of the scanning head 16. Telecentric lenses, 32A and 32B, and line sensors, 34A and 34B, are arranged parallel to the direction of image capturing line 74 (hereinafter referred to simply as the "image capturing direction"). Line 70A read by line sensor 34A and line 70B read by line sensor 34B partially overlap. If image data for one line is captured in this state, scanning head 16 moves in direction 76 by one line. Repetition of the same process steps provides two image segments having partial overlap, which is reflected in all lines [constituting the overall image] of board 1.

Telecentric lenses, 32A and 32B, are configured in such a manner that the main light at the object side is parallel to the optical axis and does not change magnification at the imaging side even though the lenses are defocused. As a result, even though components of different heights are mounted on board 1, the image of the board can be captured within the same field of view at the same magnification. For example, when a tall component like a condenser is mounted on board 1, the image thereof can be captured from right above board 1 under vertical lighting. In addition, the two telecentric lenses, 32A and 32B, allow image capture for a unified width that includes all widths wider than the field of view of the lenses.

Nonetheless, complex machining is provided to telecentric lenses, 32A and 32B, required for design of a telecentric optical system, which causes aberration derived distortions on the captured image. Packaging or etching of conductor patterns is performed on the order of tens of microns on board 1, as a result, aberration derived distortions has a serious adverse impact on inspection accuracy, necessitating correction of distortions thereof. Large distortions appear particularly at the edges of telecentric lenses 32A and 32B wherein these distortions include positional deviations and color convergence. For this reason, when two image segments are captured by the two telecentric lenses 32A and 32B, creating a partial overlap between the two image segments, the overlapping portion fails to maintain white balancing thereof and color data thus obtained do not match at the border of the two images. Even though positions are corrected, color convergence makes it difficult to correlate two image segments near the border line, thereby adversely affecting accuracy of inspection.

To overcome the above problems, the appearance inspection correction process of the present invention takes advantage of the use of a telecentric optical system as hereafter described and in the following order: (A) correction of lens aberrations within a single telecentric optical system; (B) position correction of the overlapping portion required for synthesis of two images captured by two telecentric optical systems; and (C) color correction of the overlapping portion required for synthesis of the two image segments.

(A) Correction of Lens Aberrations within a Single Telecentric Optical System

Generally, aberration derived distortions are magnified at the periphery of telecentric lenses. When an image of board 1 is captured by a telecentric optical system, aberration derived distortions are magnified toward the edge of the image. For example, when 40 pixels per 1 mm are captured at the center, the image may be reduced to 35 pixels or magnified to 45 pixels per 1 mm toward the edge. The rate of change in lens distortion adversely affects the accuracy of appearance inspection to a great extent, therefore, correction per pixel must be provided.

Figure 3:
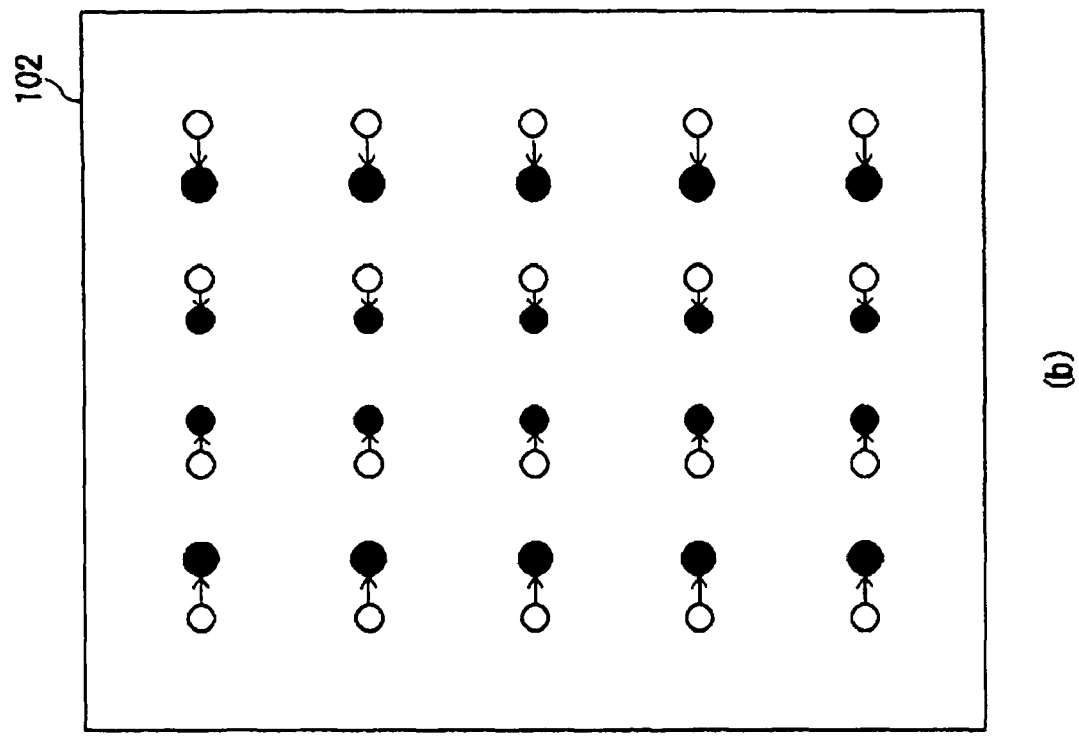
FIG. 3 is a diagram illustrating a calibration board having ID markings and a distorted image of ID markings thereof on the calibration board.
Figure 3:
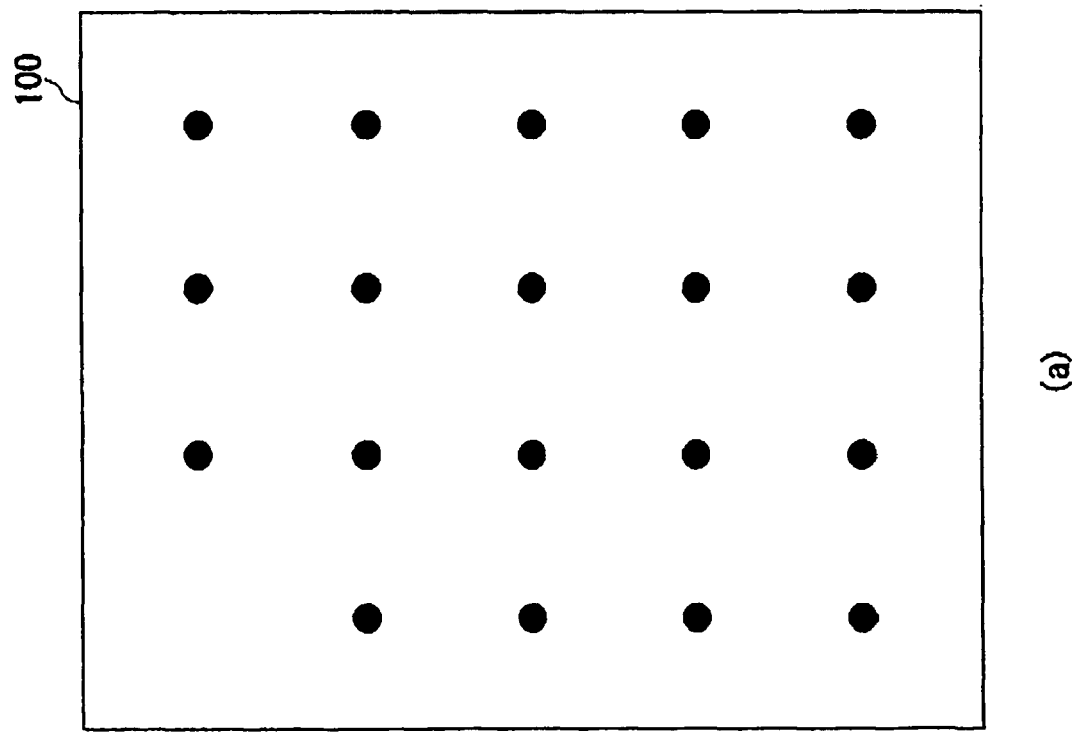

An example of correction of these aberration derived distortions is illustrated in FIG. 3(*a*): a calibration board 100 having a lattice of ID markings at every 10 mm is scanned by a telecentric optical system. FIG. 3(*b*) is a diagram illustrating two dimensional deviations of ID markings on the captured image 102 of calibration board 100. White circles denote original positions of ID markings; black circles denote positions of ID markings on an image. Arrows denote directions and magnitudes of deviation i.e. vector information; the size of black circles reflects a change in the size of ID markings. As position correction unit 45 detects a change in the vectors of ID markings based on captured image 102 of calibration board 100, it determines the amount of correction required for each pixel in the direction of the image capture line, creates a position correction table, and stores the table in correction data memory unit 49. Position correction unit 45 corrects distortions of the image of board 1 captured by the telecentric optical system on a pixel basis, based on the position correction table.

(B) Position Correction within the Overlapping Portion of Two Image Segments

Figure 4:
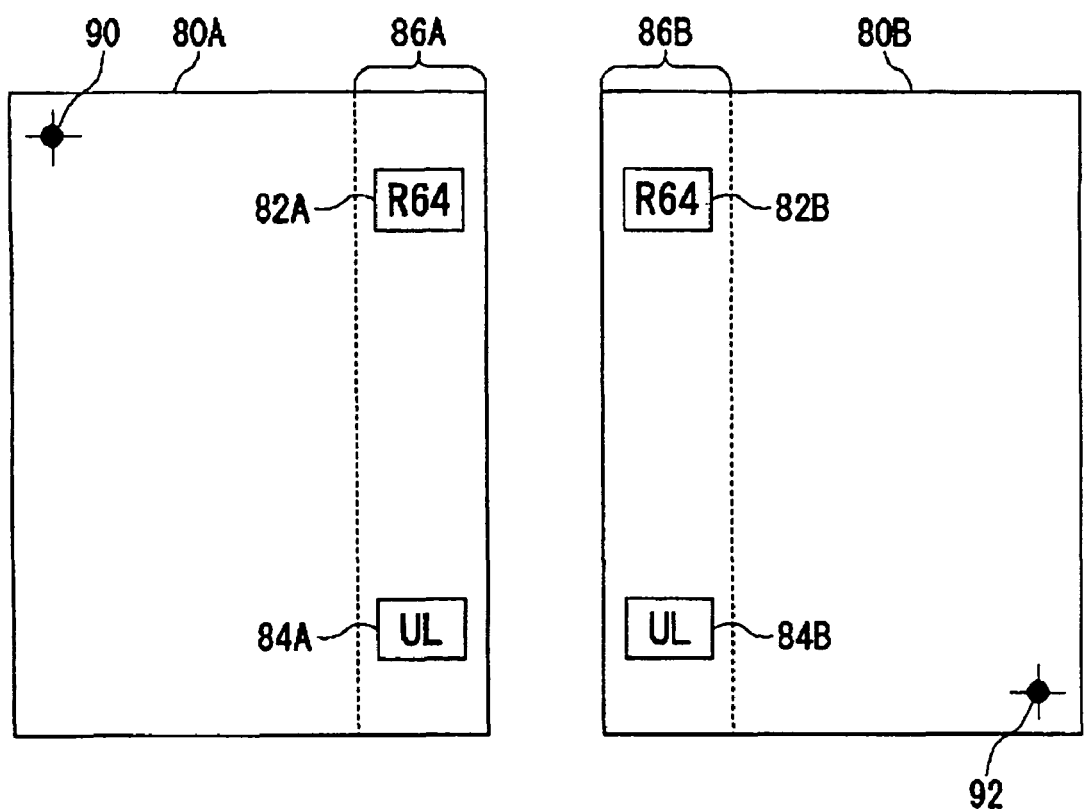
FIG. 4 is a diagram illustrating two image segments captured by two line sensors.

FIG. 4 is a diagram illustrating two pieces image segments, 80A and 80B, captured by line sensors 34A and 34B. The two image segments, 80A and 80B, are captured by line sensors 34A and 34B, corresponding to each image having overlapping portions 86A and 86B. The image of marking 90 is captured at the top left of image 80A; marking 92 is captured at the right bottom of image 80B. The markings, 90 and 92, help the line sensors 34A and 34B recognize the start point and the end point of inspection. The electronic components, 82A and 82B, have two images captured in an overlapping manner. In a similar manner, an array of characters, 84A and 84B, designating the standard or product name printed on the board also have two image segments captured in an overlapping manner. Position correction unit 45 detects these objects whose images are captured in an overlapping manner, matches two image segments, calculates the two dimensional deviations from these objects based upon using the reference points and puts the two image segments, 80A and 80B, together. A given point between two reference points must be correlated between the two images by a linear or other interpolation technique. Alternately, an object for use as a reference point may be detected at a point other than the edge of the overlapping portion to enhance the accuracy of interpolation.

(C) Color Correction within Overlapping Portion of Two Pieces of Images

Usually, the output pixel values of the image data, 54A and 54B, captured by line sensors, 34A and 34B, are determined on the assumption that the pixel values have a linear relationship with the incident luminous energy. Color correction unit 47 corrects values of pixels in the overlapping portion of the two image segments with reference to the color correction table stored in correction data memory unit 49 in advance. The color correction table is created in the following manner.

Figure 5:
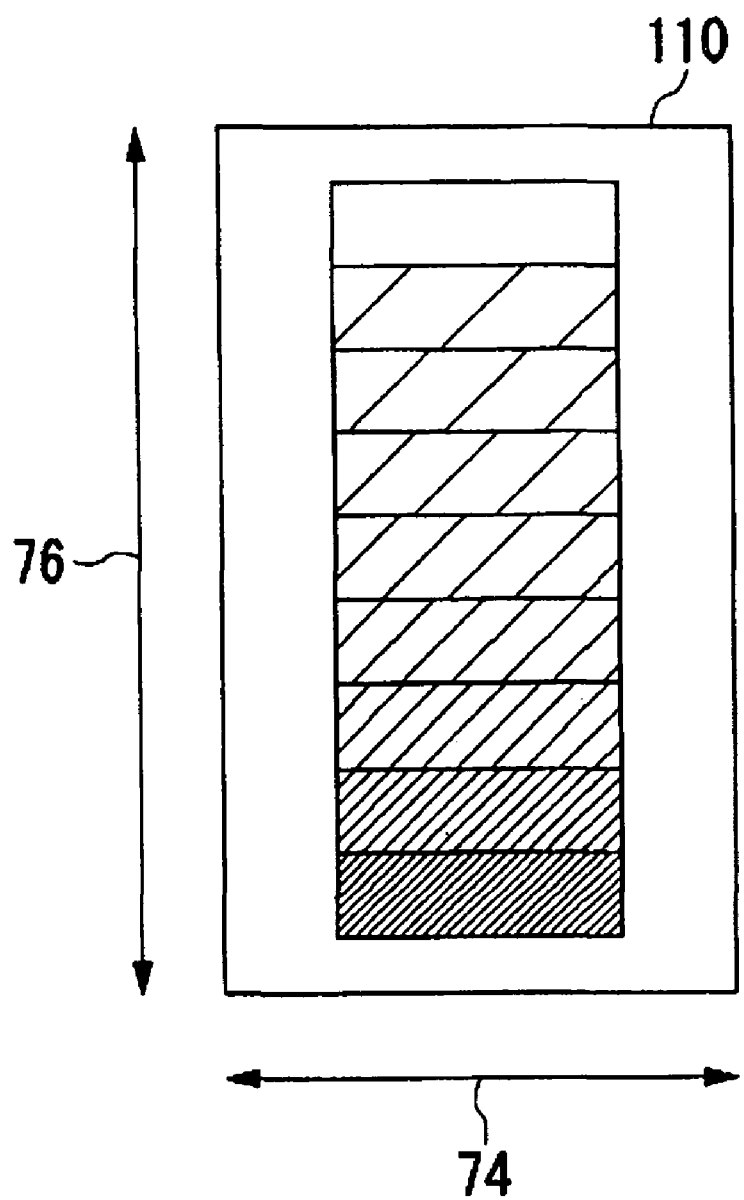
FIG. 5 is a diagram illustrating a gray scale chart for color corrections.

First, the two telecentric optical systems capture images by scanning gray scale chart 110 in which a monotone is graded from white to black. Gray scale chart 110 is provided in parallel to the directions of FIG. 5, which is the same as moving direction 76 and image capture direction 74 of scanning head 16. Here, gray scale chart 110 is provided in the center of holding base 22 such that two telecentric optical systems scan gray scale chart 11 at the edge of each lens.

Figure 6:
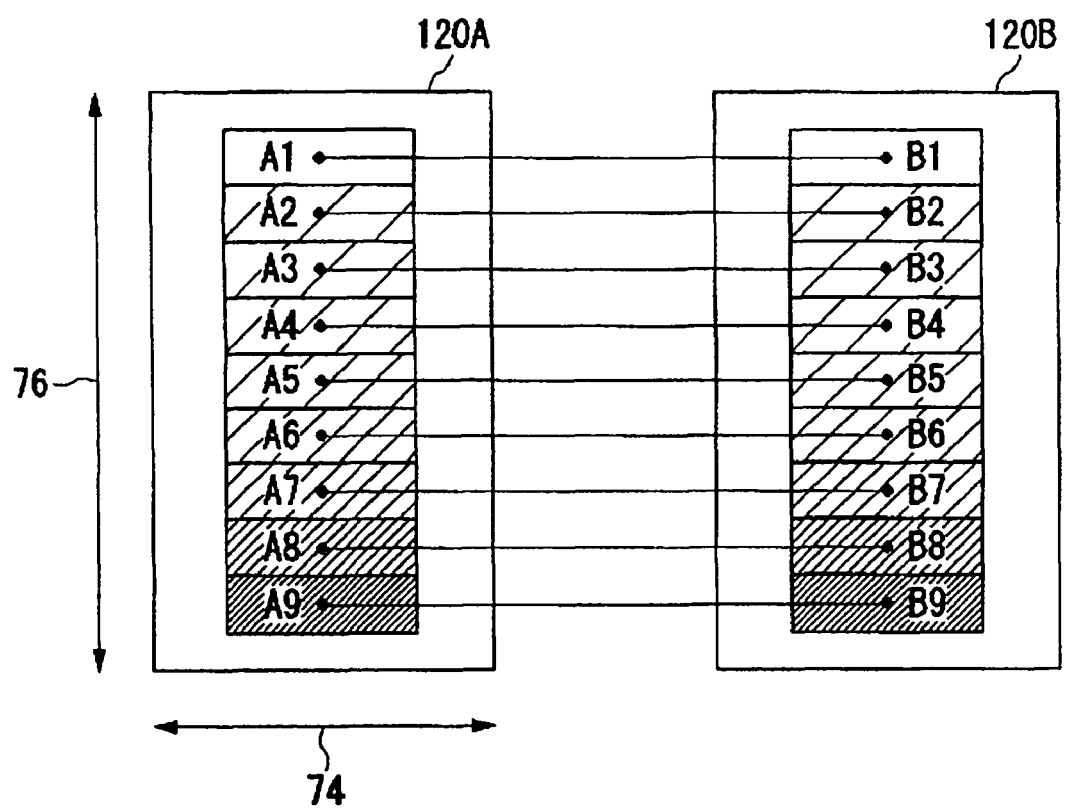
FIG. 6 is a diagram illustrating the image of the gray scale chart of FIG. 5 captured by two telecentric optical systems.

FIG. 6 illustrates images, 120A and 120B, of gray scale chart 110 whose image is captured by two telecentric optical systems. Points A1–A9 at the left end of FIG. 6 are pixel values corresponding to each grading of gray scale chart 110 obtained by a first telecentric optical system; points B1–B9 at the right end of FIG. 6 are pixel values corresponding to each grading of gray scale chart 110 at the same position [sic, grade] as Points A1–A9. In theory, these pixels should have the same values; however, they usually have different values because of lens aberrations that exist in reality. Color correction unit 47 makes necessary corrections to equate the pixel values B1–B9 of the second telecentric optical system with those of A1–A9 of the first telecentric optical system as corresponding pairs of pixel values.

Figure 7:
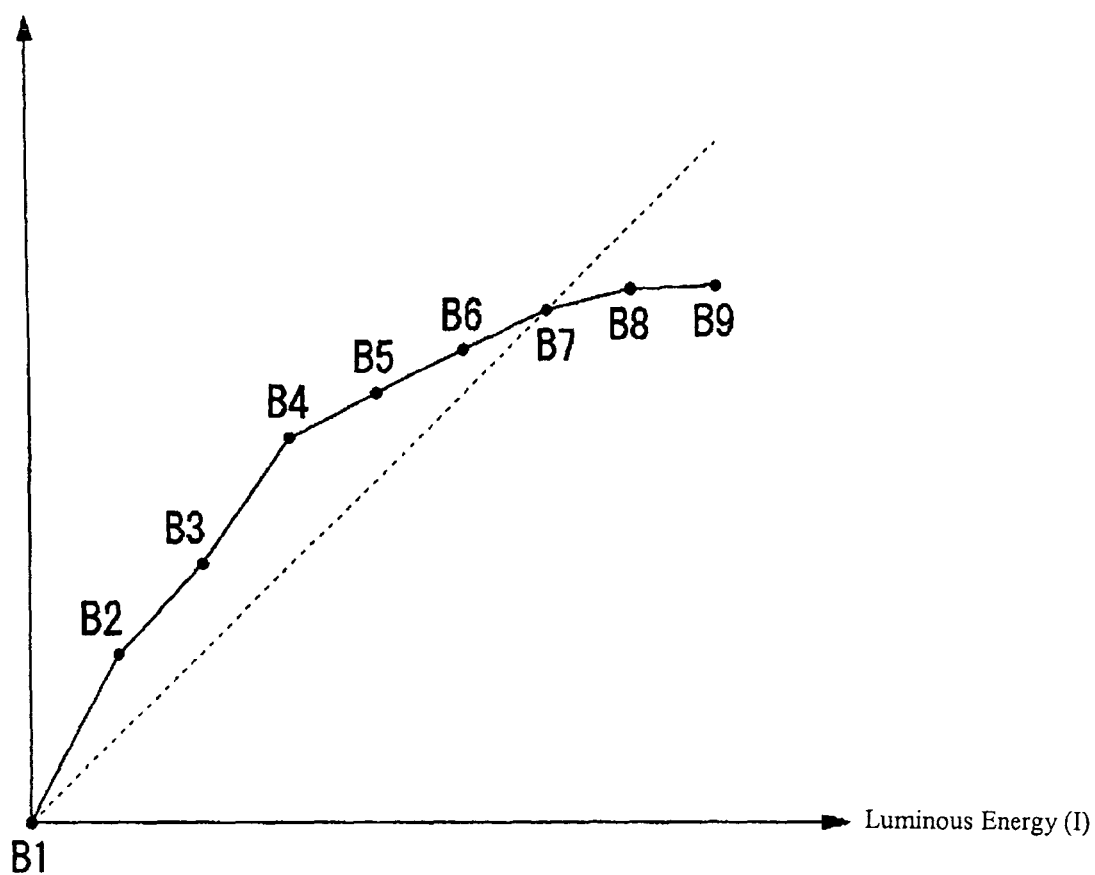
FIG. 7 is a graph of a function plotting the color corrected pixel value outputs of the telecentric optical system.

FIG. 7 is a graph plotting pixel values of the second telecentric optical system with color correction as a function of luminous energy. In the pixel value output function graph, a pixel value (P) output originally has a linear relationship with luminous energy (I) as shown by the dotted line in FIG. 7. However, it is corrected to a broken line by connecting corrected pixel values B1–B9 as shown in FIG. 6. In other words, color correction unit 47 matches the pixel output function of the second telecentric optical system with that of the first telecentric optical system. This correction is also provided in manner similar to other corresponding points in the overlapping portion of the two image segments captured by the two telecentric optical systems such that pixel values in the overlapping portion match between the two telecentric optical systems. Color correction values of the overlapping portion thus obtained is stored in correction data memory unit 49 by color correction unit 47.

Procedures for appearance inspection utilizing the appearance inspection apparatus 10 having the above configuration are described below. The appearance inspection procedure can be divided into a calibration step illustrated in FIG. 8 and an inspection step illustrated in FIG. 9. Usually, calibration of appearance inspection apparatus 10 is performed when it is used for the first time while an inspection is performed afterwards.

Figure 8:
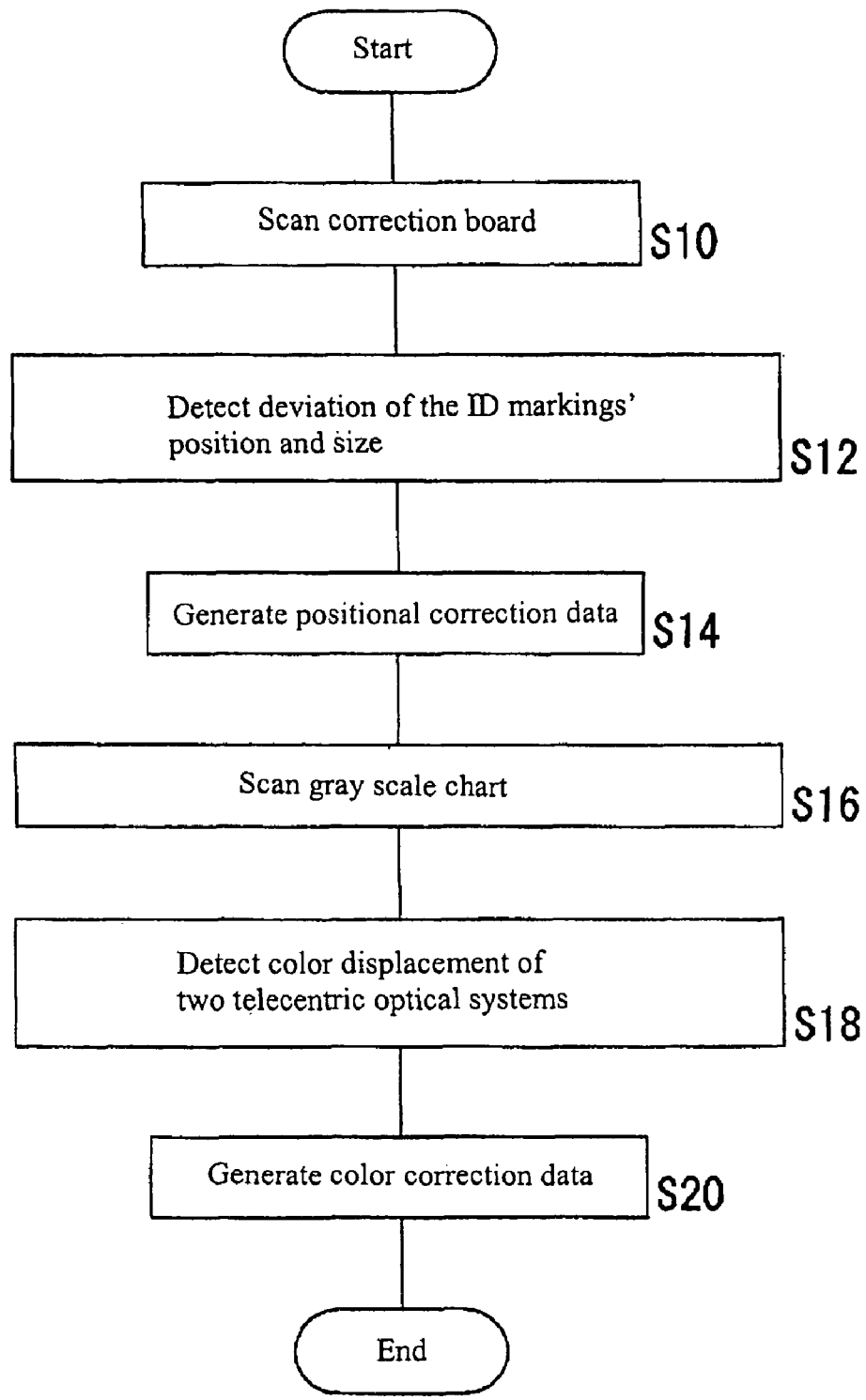
FIG. 8 is a flow chart illustrating the calibration steps for the appearance inspection method for the embodiment of FIG. 1.

During the calibration process illustrated in FIG. 8, scanning head 16 obtains image data by scanning a calibration board and stores the data in memory 44 (S 10). Position correction unit 45 detects, from the image of the calibration board stored in memory 44, the position and size of ID markings based on the image of the calibration board stored in memory 44, to determine the magnitude of deviations of ID markings from the reference position where the ID markings should actually be and from the size the markings should actually be (S12). Position correction unit 45 creates position correction data required for correcting distortions of ID markings and stores the data in correction data memory unit 49 (S 14).

Next, scanning head 16 scans a gray scale chart and captures two image segments by two telecentric optical systems to store the data in memory 44 (S 16). Color correction unit 47 detects color convergence of the two telecentric optical systems (S 18) and creates color correction data required for correcting color convergence and stores the data in correction data memory unit 49 (S 20).

Figure 9:
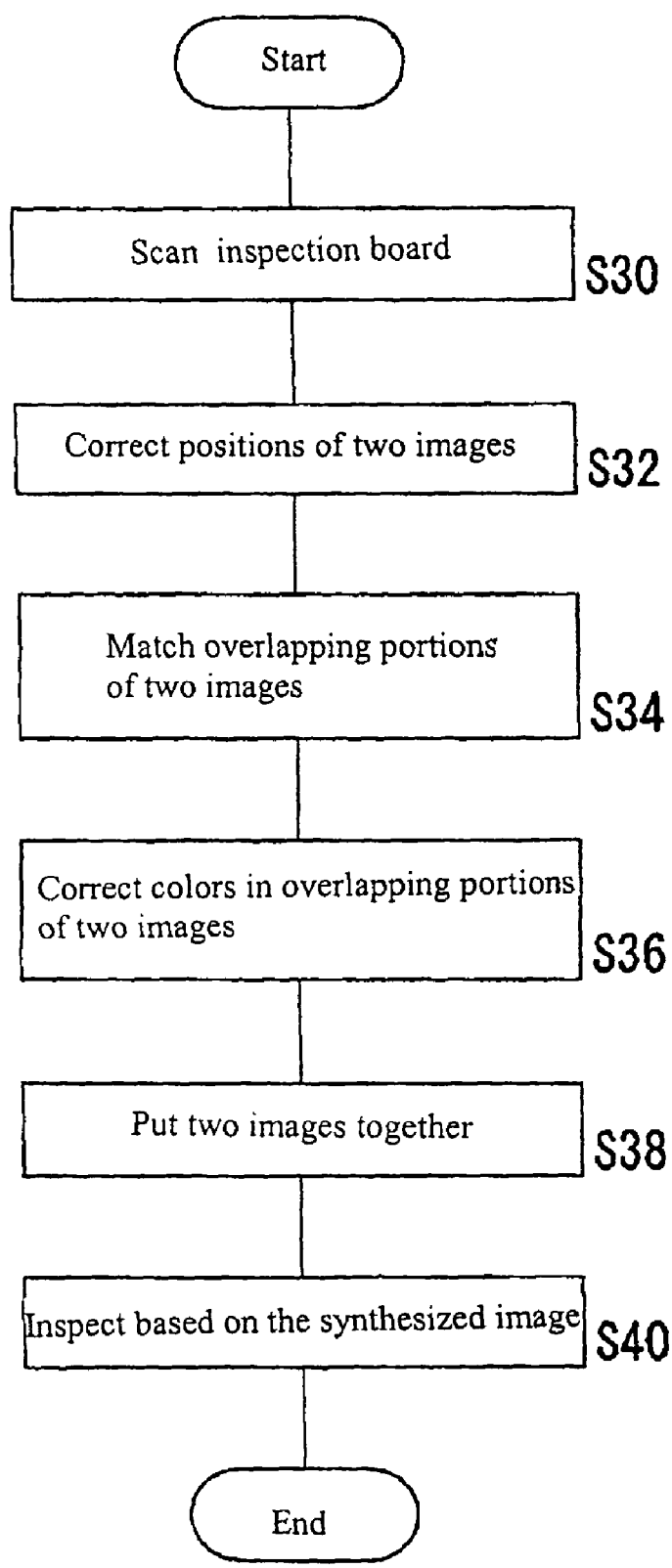
FIG. 9 is a flow chart illustrating the inspection steps of the appearance inspection procedure for the embodiment of FIG. 1.

In the inspection process as illustrated in FIG. 9, scanning head 16 scans board 1, to obtain data for two image segments and stores the data in memory 44 (S 30). Position correction unit 45 corrects distortions such as lens aberration derived displacement appearing at arbitrary points in the two image segments and stores the corrected data in memory 44 (S 32). Then, positional correction unit 45 detects positions of the reference subject points in the overlapping portion of the two image segments stored in memory 44 to correct deviations at points in the overlapping portions such that positions of reference subject points match between the image segments (S34).

Color correction unit 47 further corrects color convergence of the overlapping portions of the two image segments, with reference to the color correction table stored in correction data memory unit 49, thereby storing the corrected data in memory 44 (S 36). Image processing unit 43 creates a combined or synthesized image by putting the two image segments together and stores the combined synthetic image in memory 44 (S38). Analysis unit 46 determines pass or failure of the board 1 with reference to the evaluation standard stored in evaluation standard memory unit 48 for each inspection item prepared for points to be inspected based on the synthetic image stored in memory 44 (S 40). For example, in the missing component inspection, presence or absence of a component is checked based on the brightness of pixels that are present in a specific region on an image where the component should be present. During soldering inspection, pass or failure of soldering is checked by sizing the area of bright pixels in a region on an image including the soldered points. In the displacement test, displacement of components is determined based on the brightness of the region on the image including electrode patterns at the outer circumference of the component.

As described above, the appearance inspection system of this embodiment captures two separate images of a board utilizing two telecentric optical systems and performs inspection based on a synthesized image made by correcting displacements near the border of the two images. The apparatus can, therefore, perform inspection of a large sized board at once based on the synthetic image data. This apparatus thus allows the use of line sensors available in the market to perform an appearance inspection without ordering customized line sensors having a large number of pixels that correspond to the width of the board. In addition, it allows easier and more accurate inspection than the method of inspecting two image segments separately. The use of telecentric lenses allows the apparatus to capture images of a board having components of different heights mounted thereon from immediately above the aboard under vertical lighting, thereby allowing the apparatus to inspect all components at one time.

Embodiments of the present invention were described above. These embodiments represent some of the possible examples. It is apparent to anyone of ordinary skill in the art to understand that each constituting element or combinations of data processing may be modified in many ways and these modifications remain within the spirit of the present invention.

Such modifications include as follows: instead of capturing two image segments, utilizing two sets of telecentric optical systems according to the above embodiment, three images may be captured with some overlapping portions utilizing three or more sets of telecentric optical systems. Alternately, a half of the board may be scanned by a set of telecentric optical systems, and the same optical system may be moved along the image capture line to capture another half of the board by scanning in the opposite direction. The reciprocal movements of the above motions provide two image segments, which can further synthesized to obtain an overall image of the board, even though this is a time consuming method.

In the above color correction, a color correction table is prepared utilizing a gray scale chart whose image is captured by two telecentric optical systems. However, the gray scale may be eliminated: the pixel values of the first telecetnric optical system may be corrected with reference to the pixel values of the second telecentric optical system to cancel color convergence. The same color correction method may be used in this case as well.

REFERENCE SYMBOLS

1 board
10 appearance inspection apparatus
12 main unit
14 test unit
16 scanning head
30 lighting unit
32A, 32B telecentric lenses
34A, 34B line sensors
40 head control unit
42 memory control unit
44 memory
43 image processing unit
45 position correction unit
46 analysis unit
47 color correction unit
48 evaluation standard memory unit

What is claimed is:

1. An appearance inspection apparatus comprising:
   a scanning head for scanning a board surface of a body to be inspected to capture an image thereof; and
   a main unit for inspecting the captured image;
   wherein said scanning head further comprises:
      at least one telecentric lens and at least a corresponding number of one-dimensional line sensors in an arrangement parallel to the image capturing direction such that each telecentric lens forms an image of reflected light reflected from said board surface and each one-dimensional sensor captures catoptrical light and that each one-dimensional sensor captures an image segment of the board surface for forming a partially overlapping portion; and
   wherein said main unit further comprises:
      an image processing unit that assembles the images captured by each of said liner sensors after calibrating pixel data in said overlapping portion and attaches the images together; and
      an analysis unit that inspects an image segment with reference to a given evaluation standard to determine pass or failure for each inspection item.

2. The appearance inspection apparatus as set forth in claim 1 wherein said image processing unit includes a color correction unit that corrects color convergence occurring in color data pixels in said overlapping portion.

3. The appearance inspection apparatus as set forth in claim 2 wherein said color correction unit adjusts a color correction table of a second telecentric lens with reference to a color correction table of a first telecentric lens such that color data of pixels in said overlapping portion matches that of said first telecentric lens.

4. The appearance inspection apparatus as set forth in claim 3 wherein color correction data is generated in advance for correcting chromatic aberrations of said telecentric lenses at the edge of said telecentric lens such that color convergence of said overlapping portion is corrected based on said color correction table image captured by said scanning head.

5. The appearance inspection apparatus as set forth in claims 4 wherein said image processing unit further comprises a position correction unit for alignment that is based on reference data included in said overlapping portion.

6. A method of inspecting appearance comprising:
   capturing images of a board to be inspected utilizing multiple telecentric lenses in such a manner that the captured images partially overlap;
   putting together said images after correcting for color convergence in said overlapped portion; and
   performing a given inspection based on said synthesized image.

* * * * *